(12) United States Patent
Svendsen et al.

(10) Patent No.: US 6,817,989 B2
(45) Date of Patent: Nov. 16, 2004

(54) NEEDLE COVERING MECHANISM, NEEDLE HOLDER AND HYPODERMIC SYRINGE

(75) Inventors: Terje Svendsen, Asker (NO); Jon Myhre, Stjordal (NO)

(73) Assignee: Syringus AS, Oslo (NO)

( * ) Notice: Subject to any disclaimer, the term of this patent is extended or adjusted under 35 U.S.C. 154(b) by 141 days.

(21) Appl. No.: 10/311,689

(22) PCT Filed: Jun. 25, 2001

(86) PCT No.: PCT/NO01/00268

§ 371 (c)(1),
(2), (4) Date: Dec. 19, 2002

(87) PCT Pub. No.: WO02/00277

PCT Pub. Date: Jan. 3, 2002

(65) Prior Publication Data

US 2004/0044312 A1 Mar. 4, 2004

(30) Foreign Application Priority Data

Jun. 23, 2000 (NO) .............................. 003309

(51) Int. Cl.⁷ ............................. A61M 5/00; A61M 5/32
(52) U.S. Cl. ...................................... 604/192; 604/198
(58) Field of Search .............................. 604/181, 187, 604/192, 198, 231, 236, 237, 238, 240, 244, 264, 265, 905, 907; 128/919

(56) References Cited

U.S. PATENT DOCUMENTS

| 5,049,133 A | | 9/1991 | Villen Pascual |
| 5,053,010 A | | 10/1991 | McGary et al. |
| 5,122,118 A | | 6/1992 | Haber et al. |
| 5,188,614 A | | 2/1993 | Hart |
| 5,304,137 A | * | 4/1994 | Fluke .......................... 604/110 |
| 5,360,408 A | * | 11/1994 | Vaillancourt ................. 604/198 |
| 5,411,487 A | | 5/1995 | Castagna |
| 6,267,748 B1 | | 7/2001 | Gulliksen et al. |
| 6,716,197 B2 | * | 4/2004 | Svendsen ..................... 604/192 |

FOREIGN PATENT DOCUMENTS

| WO | WO 92/05818 | 4/1992 |
| WO | WO 98/30261 | 7/1998 |
| WO | WO 01/47588 | 7/2001 |

* cited by examiner

Primary Examiner—Michael J. Hayes
Assistant Examiner—Matthew DeSanto
(74) Attorney, Agent, or Firm—Young & Thompson

(57) ABSTRACT

A needle covering mechanism for a hypodermic syringe includes a protective cover sleeve which is movable between a retracted position in which a needle is exposed and an extended position in which the needle is covered. A retainer includes first detents which by means of a spacer is forced to engage indentations in the cover sleeve to prevent a movement of the cover sleeve towards the extended position. The spacer is made from a material which after some time in contact with an injectant loses its mechanical strength, and some time after filling the syringe with an injectant, the spacer deforms, the first detents slip out of the indentations in the cover sleeve, and a spring forces the cover sleeve to the extended position.

15 Claims, 11 Drawing Sheets

US 6,817,989 B2

NEEDLE COVERING MECHANISM, NEEDLE HOLDER AND HYPODERMIC SYRINGE

FIELD OF THE INVENTION

The invention relates to a needle covering mechanism for a hypodermic syringe comprising a barrel for an injectant and a plunger for expelling the injectant from the barrel, the needle covering mechanism comprises a protective cover sleeve which is movable between a retracted position in which a needle is exposed and an extended position in which the needle is covered, a helical compression spring located inside the cover sleeve for biasing the cover sleeve towards the extended position, a lock for keeping the cover sleeve in the retracted position, and a release mechanism for releasing the lock.

The invention also relates to a needle holder for a hypodermic syringe, which needle holder comprises a needle covering mechanism The invention further relates to a hypodermic syringe comprising a barrel and a plunger, which syringe comprises a needle covering mechanism.

BACKGROUND OF THE INVENTION

Needles of used syringes constitute a risk, both by themselves and as a source to contagion. Re-use of syringes constitutes a particular risk for contagion.

Most syringes are disposable syringes with a standardised fitting which can mate corresponding standardised fittings of syringe needles. This standardised fitting enables a wide range of combinations of various syringe sizes and needle sizes. A common standardised fitting is the Luer fitting.

Various safety syringes, in which the needle is retracted or covered after use are known.

U.S. Pat. No. 5,122,118 describes an automatic needle retracting syringe in which a gelatine capsule retains a helical spring. Upon contact with the liquid injectant, the gelatine capsule weakens and allows the spring to retract the needle into the body of the syringe.

U.S. Pat. No. 5,049,133 describes a manual needle retracting syringe in which a spring which can retract the needle into the body of the syringe is releasable by moving the plunger to trigger a plurality of teeth-shaped hinges.

U.S. Pat. No. 5,188,614 describes a protective casing for use with a hypodermic syringe. A dual component foaming agent is disposed in the casing. When the components are mixed together they form an expanding and hardening plastic foam. Upon pressing the syringe into the casing subsequent to the ejection of fluid from the syringe, the foaming agents are activated and the expanding foam forces the syringe and syringe needle rearwardly within the casing, and encapsulates the used needle within the casing and foam.

U.S. Pat. No. 5,411,487 describes a needle covering mechanism for a hypodermic syringe comprising a barrel for an injectant and a plunger for expelling the injectant from the barrel, the needle covering mechanism comprises a protective cover sleeve which is movable between a retracted position in which the needle is exposed and an extended position in which the needle is covered, a helical compression spring located inside the cover sleeve for biasing the cover sleeve towards the extended position, a lock for keeping the cover sleeve in the retracted position, and a manual release mechanism for releasing the lock.

WO-A-9 205 818 describes a needle retracting syringe in which a spring which forces the needle into the plunger is released by pressing the plunger into the barrel after use.

WO 98/30261 describes a needle holder for use in combination with a syringe and a needle. The needle holder is provided with an expandable element and retention means for the expandable element. Contact between the expandable element and an injectant causes the expandable element to expand and retract the needle into the needle holder.

Prior art automatic safety syringes which function by a response to the injectant, i.e. essentially water, are generally encumbered with an unreliable and unpredictable release of the actuator.

Prior art manual safety syringes arm generally encumbered with the drawback that the force which is required to release the actuator is so large that using the safety syringe is felt cumbersome.

In some of the above mentioned safety syringes the needle and the protection mechanism are integrated in the syringe barrel. There is therefore no possibility of combining variable syringe sizes with various needle sizes, which means that a greater number of syringe variants must be held in stock to satisfy all needs. Logistically this is a big problem.

A favourable material which respond to the injectant is alginate, which loses its mechanical strength and eventually dissolves in water. Alginate items are formed by extrusion or moulding. The resulting items are however fragile and mechanically weak, and may deform when subjected to forces for a long period, which means that they easily deform or break. From this point of view, alginate is therefore not a preferable material.

NO 19996459 describes an automatic needle retracting mechanism for a hypodermic syringe comprising a body which slidingly supports a needle. A retainer for an actuator and the needle is kept in a retaining position by a spacer, preferably made from alginate, which after some time in contact with an injectant loses its mechanical strength. A filing of the needle with an injectant causes a deformation of the spacer, a release of the actuator and a retracting of the retainer and needle into a needle retraction chamber. The needle retracting mechanism may also include an inner sleeve which is manually movable towards the retainer for a manual release of the actuator. The needle retracting mechanism may be included in a needle holder or be integrated in a syringe.

In the automatic needle retracting mechanism of NO 19996459, many of the above problems are solved. The automatic needle retracting mechanism of NO 19996459 is however encumbered with the drawback that the dead volume, which contains injectant residues after the injection, is big.

SUMMARY OF THE INVENTION

The object of the invention is to provide an improved safety syringe in which the above problems are reduced or eliminated. Another object is to provide a safety syringe with both an automatic and a manual release. A further object is to provide an automatic safety syringe in which alginate is suitable as material in the injectant responding item.

The objects are achieved by a needle covering mechanism, a needle holder and a hypodermic syringe according to the preamble, which are characterized by the features of the claims.

In a first aspect the invention thus relates to a needle covering mechanism for a hypodermic syringe comprising a barrel for an injectant and a plunger for expelling the injectant from the barrel. The needle covering mechanism comprises a protective cover sleeve which is movable between a retracted position in which a needle is exposed and the syringe is operable, and an extended position in which the needle is covered and the syringe is protected. According to the invention, the protective sleeve is kept in the retracted position by a lock which is automatically releasable by contact with the injectant. Preferably the lock is also manually releasable by pushing the plunger into the bottom of the barrel.

In a second aspect the invention relates to a needle holder which is adapted to match an outlet from a hypodermic syringe, and which comprises the needle covering mechanism according to the invention. This needle holder may be used for injections or to withdraw bodily fluids, fitted to a hypodermic syringe, or fitted to another purpose designed apparatus.

In a third aspect the invention relates to a hypodermic syringe comprising a plunger and a barrel, in which the needle covering mechanism according to the invention forms an integral extension.

BRIEF DESCRIPTION OF THE DRAWING

The invention will now be explained in closer detail with reference to the enclosed drawings, in which.

DETAILED DESCRIPTION OF THE DRAWING

Figure 1:
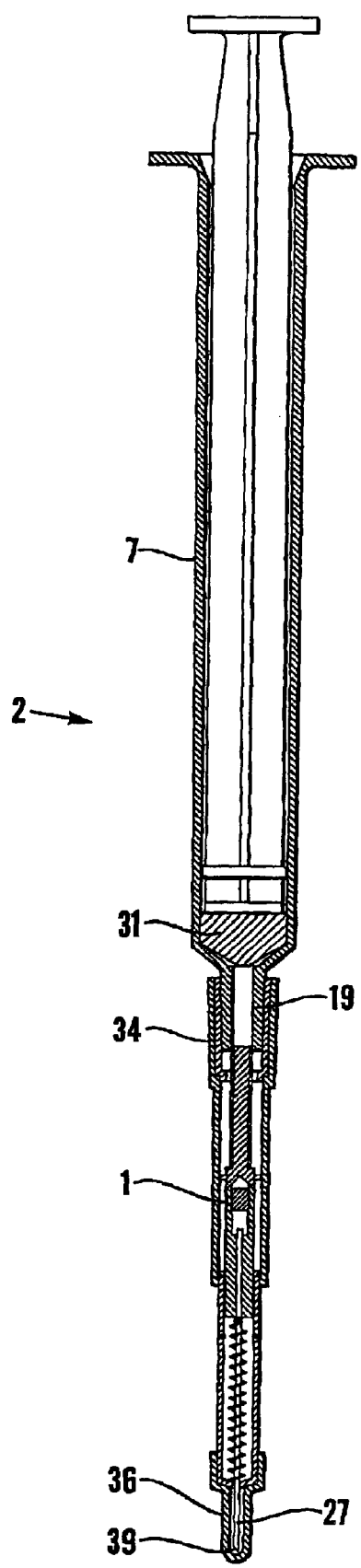
FIG. 1 illustrates a hypodermic syringe with a needle holder comprising a needle covering mechanism according to the invention, a cover sleeve being in a storage position.

FIG. 1 illustrates a hypodermic syringe 2 comprising a barrel 7 for an injectant and a plunger 31 for expelling the injectant from the barrel 7 through an outlet 19. A needle holder 34 with a needle 27 and an automatic needle covering mechanism 1 according to the invention is fitted on the outlet 19. A protective cap 36 protects personnel against the needle tip 39. The syringe 2 is a disposable syringe which is available in various sizes, with the outlet 19 designed as a standard Luer fitting. The needle holder 34 may be used for various syringes with standard fittings. The needle holder 34 may also be fitted to vials or purpose designed apparatuses for withdrawal of bodily fluids.

Figure 2:
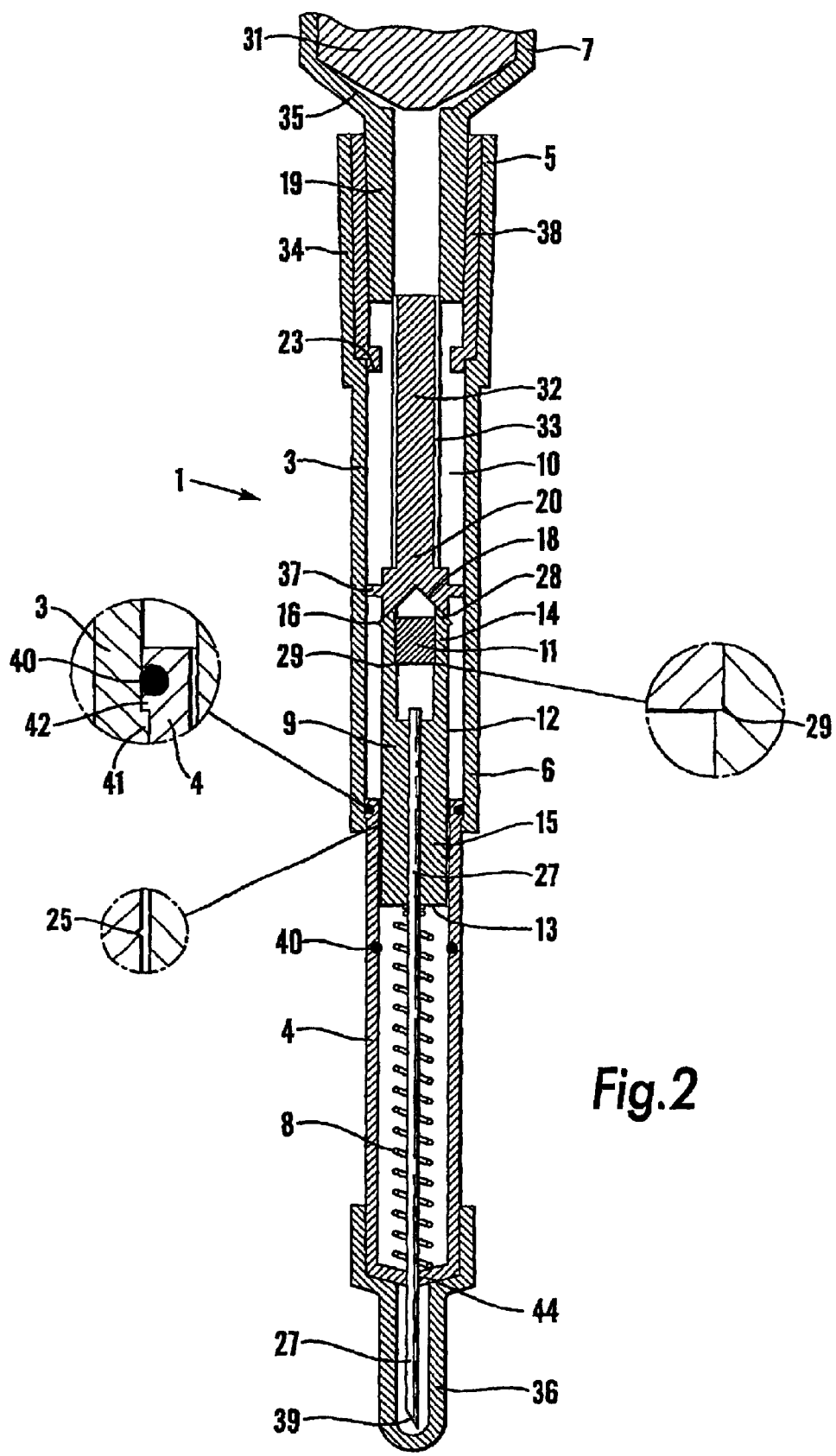
FIG. 2 illustrates the needle holder in FIG. 1 in a larger scale.

FIG. 2 illustrates the needle holder 34 in FIG. 1 in a larger scale. The needle covering mechanism 1 comprises a body 3 with a cover sleeve retraction chamber 10 for accommodating a protective cover sleeve 4 which is slidingly supported inside the body 3. A first end 5 of the body 3 is adapted to fit the outlet 19 of the syringe barrel 7, in order to receive injectant from the syringe barrel 7 during use. A liner 38 is located between the body 3 and the outlet 19, which is for the purpose of enabling production of the needle holder 34. Alternatively, the first end 5 of the body 3 may be adapted to fit the inlet of a not illustrated vial or apparatus for withdrawal of bodily fluids.

In a second end 6 the body 3 has an opening for the cover sleeve 4, enabling movement of the cover sleeve 4 between a retracted position essentially inside the retraction chamber 10, in which position of the cover sleeve the needle 27 is exposed, and an extended position, which is illustrated in FIGS. 1 and 2. A helical compression spring 8 is located inside the cover sleeve 4 for biasing the cover sleeve 4 towards the extended position. Indentations 25 in the cover sleeve 4 will be discussed later.

A retainer 9 for the cover sleeve 4, slidingly supported inside the cover sleeve 4, comprises an external sliding surface 12, a base portion 15 for fixing and supporting the needle 27, an abutting portion 13 for the helical spring 8, and a first radially compressible portion 14 with first detents 16 which in a non-compressed position projects radially out from the sliding surface 12 of the retainer 9 and in a compressed position are flush with or within the sliding surface 12.

Further the needle covering mechanism comprises a spacer 11 which is located in mountings 29 in the first radially compressible portion 14 of the retainer 9 for keeping the first radially compressible portion 14 in the non-compressed position. A trigger 20, which is slidingly supported inside the body 3, comprises a funnel-shaped portion 18 facing the first radially compressible portion 14 of the retainer 9. The spacer 11 is made from a material which after some time in contact with the injectant loses its mechanical strength, which will be discussed in more detail later.

FIGS. 1 and 2 illustrates the needle covering mechanism in a storage position in which the cover sleeve 4 is located in its extended position, and the spring 8 is relaxed. A nose 41 of the body 3 and a corresponding nose 42 of the cover sleeve 4 prevents the cover sleeve from moving beyond the extended position. The retainer 9 is located near the second end 6 of the body 3, and the needle 27 with the tip 39 projects out from the end of the cover sleeve 4 through an opening 44. As mentioned, a protective cap 36 which covers the needle tip 39 is fitted at the end of the cover sleeve 4.

The trigger 20 is located essentially in the middle of the body 3, and the funnel-shaped portion 18 of the trigger abuts the first radially compressible portion 14 of the retainer 9. The trigger 20 comprises a rod 32 which in the storage position in FIGS. 1 and 2 is located just outside the barrel outlet 19 or in an end portion of the barrel outlet 19.

In storage no injectant is present, and the spacer 11 maintains its mechanical strength and shape, which means that the first detents 16 is maintained in their position radially projecting out from the sliding surface 12 of the retainer 9.

Figure 3:
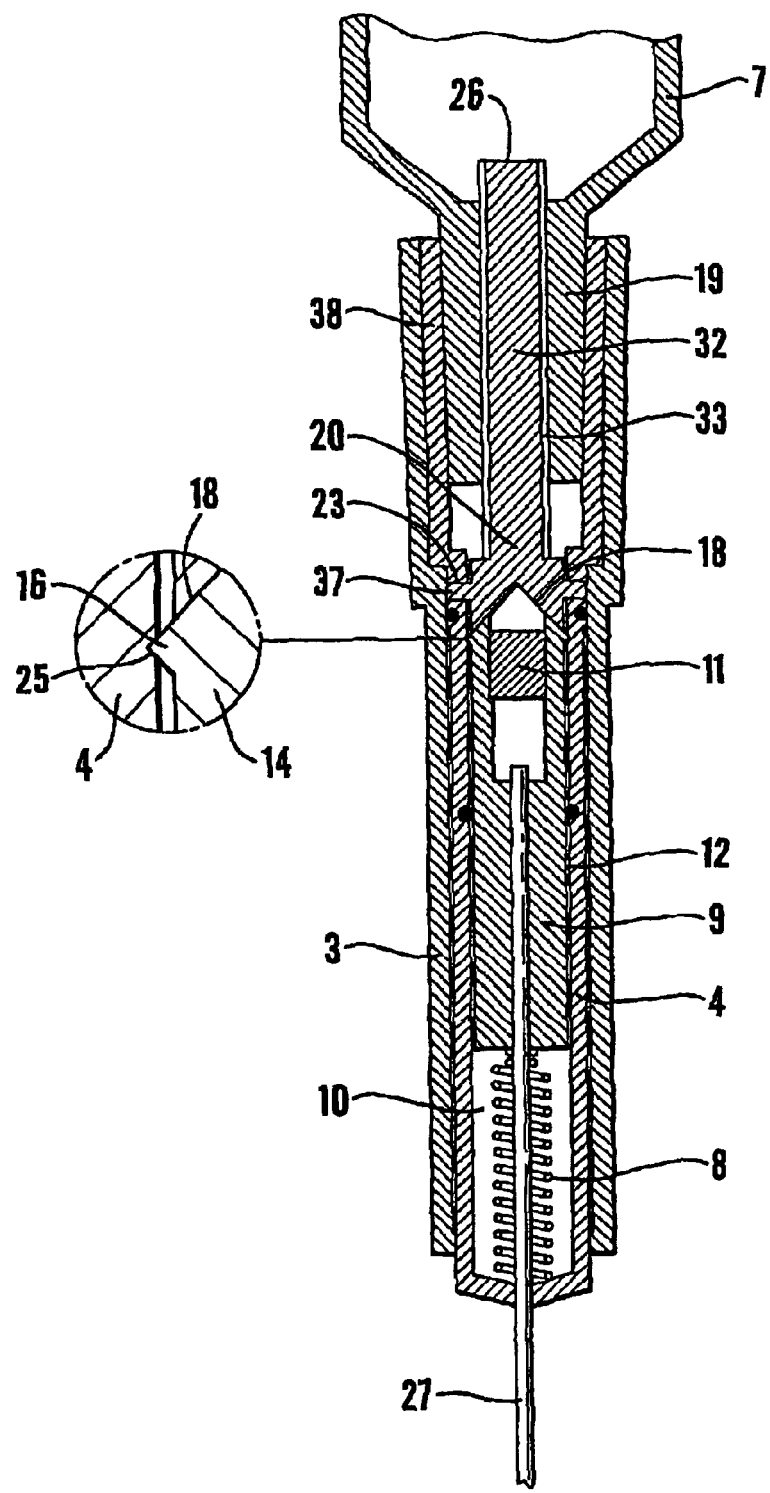
FIG. 3 illustrates the needle holder in FIG. 2 with the cover sleeve in a retracted position.

For preparation for use, the protective cap 36 is removed, and the cover sleeve 4 is manually withdrawn to the retracted position essentially inside the retraction chamber 10, which is illustrated in FIG. 3. The compression spring 8 is tensioned and moves the retainer 9 with the needle 27 into the body 3. The spring 8 biases the first radially compressible portion 14 of the retainer 9 towards the funnel-shaped portion 18 of the trigger 20, and the retainer 9 thus moves the trigger 20 towards the syringe barrel 7. The trigger rod 32 moves in through the barrel outlet 19, and extend into the barrel 7, the end of the rod 32 thereby forming a trigger head 26. The rod 32 is provided with splines 33 providing channels for the injectant.

When the trigger 20 reaches the position in FIG. 3, guides 37 of the trigger abuts stoppers 23 fixed relative to the body 3, preventing a further movement of the trigger 20 towards the syringe barrel 7. In FIG. 3, the stoppers 23 are formed by the end of the liner 38, which is fit to the body 3 and the outlet 19 of the syringe barrel 7, and thereby forms a fixed stopper.

The cover sleeve 4 is made from a flexible material, and thus a movement of the retainer 9 from the extended position in FIG. 2, through the cover sleeve 4, is possible despite the first detents 16 of the first radially compressible portion 14 of the retainer 9 project out from retainer's sliding surface 12. When the retainer 9 reaches the position in FIG. 3, the first detents 16 snap into the indentations 25 in the cover sleeve 4. The force from the spring 8 is not big enough to overcome the holding forces between the indentations 25 and the first detents 16, and the cover sleeve 4 is therefore maintained in the retracted position in FIG. 3 after the manual force which has moved the cover sleeve 4 into the retracted position has stopped.

Figure 4:
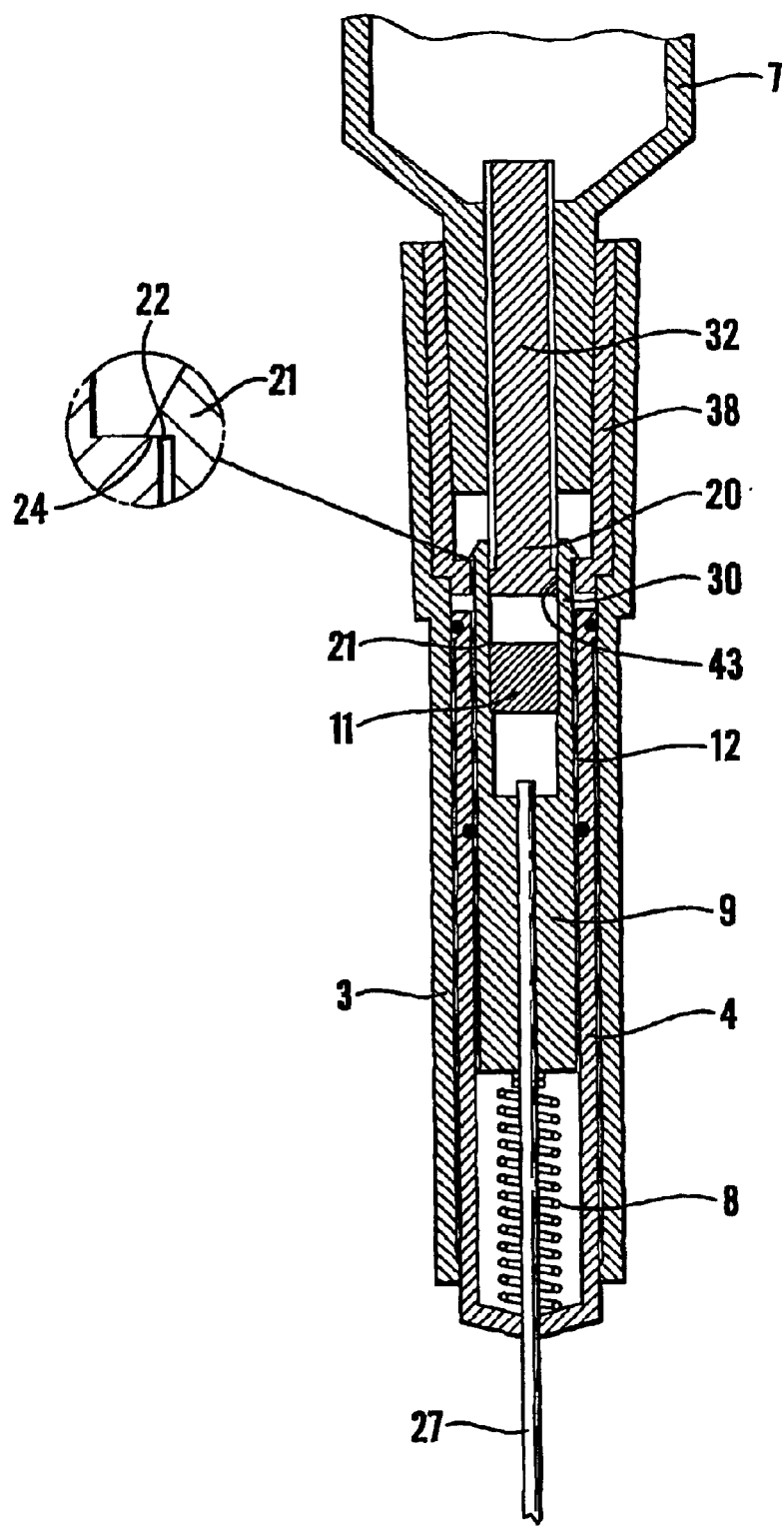
FIG. 4 illustrates the needle holder in FIG. 3 in a view perpendicular to the view of FIG. 3.

FIG. 4 illustrates the needle holder in FIG. 3 in a view perpendicular to the view of FIG. 3. It is here illustrated that the retainer 9 also comprises a second radially compressible portion 21 with second detents 22 which in a non-compressed position projects radially out from the sliding surface 12 of the retainer 9 and in a compressed position are flush with or within the sliding surface 12. The trigger 20 has a sliding surface 43 which abuts the inside of the second radially compressible portion 21, and biases the second detents 22 into the non-compressed position. The flexibility of the cover sleeve 4 allows the second detents 22 to project out from the retainer's sliding surface 12 during the movement of the retainer 9 from the storage position in FIG. 2 to the position in FIGS. 3 and 4. When the retainer 9 reaches the position in FIG. 4, the second detents 22 engage indentations 24 fixed relative to the body 3, preventing a movement of the retainer 9 away from the syringe barrel 7.

In FIGS. 3 and 4 the needle covering mechanism has assumed its operating position, i.e. the needle 27 is operable and the syringe can be used for injection.

Figure 5:
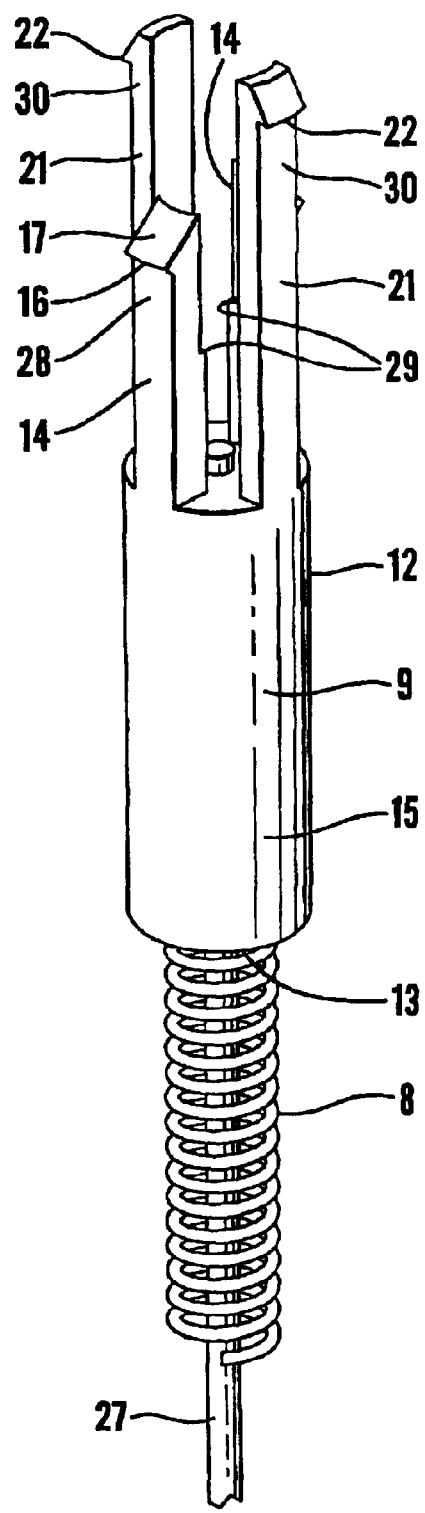
FIG. 5 illustrates a retainer according to the invention.

FIG. 5 illustrates the retainer 9, the needle 27 and the spring 8 in FIGS. 1–3 in a perspective view. The first radially compressible portion 14 of the retainer 9 comprises two first elastic arms which extend from the base portion 15 of the retainer 9 and in their free ends 28 are moveable between the compressed and non-compressed position. The first detents 16 are seen in the free ends 28 of the first elastic arms. The spacer 11 may have the form of a bolt which is adapted to fit in between the mountings 29, which are formed by steps in the first elastic arms.

The second radially compressible portion 21 of the retainer 9 similarly comprises two second elastic arms which extend from the base portion 15 of the retainer 9 and in their free ends 30 are moveable between the compressed and non-compressed position. The second detents 22 are seen in the free ends 30 of the second elastic arms.

Several retainer and spacer designs are conceivable. It is, however, required that the retainer and spacer do not prevent the injectant from flowing to the inlet of the needle 27. This requirement is met by the spacer and retainer design discussed above, since the injectant can pass between the first and second elastic arms 14, 21, besides the spacer 11.

Prior to use, the syringe barrel 7 is filled with an injectant through the needle 27 by pulling the plunger 31 backwards. O-rings 40 prevent undesired leakage of injectant. A contact between the spacer 11 and the injectant takes place, and after some time, which can be adjusted by selecting the right properties of the spacer, the injectant causes the spacer 11 to lose its mechanical strength. A typical time before the spacer loses its mechanical strength is 5 minutes, which is normally more than required for setting an injection.

Figure 6:
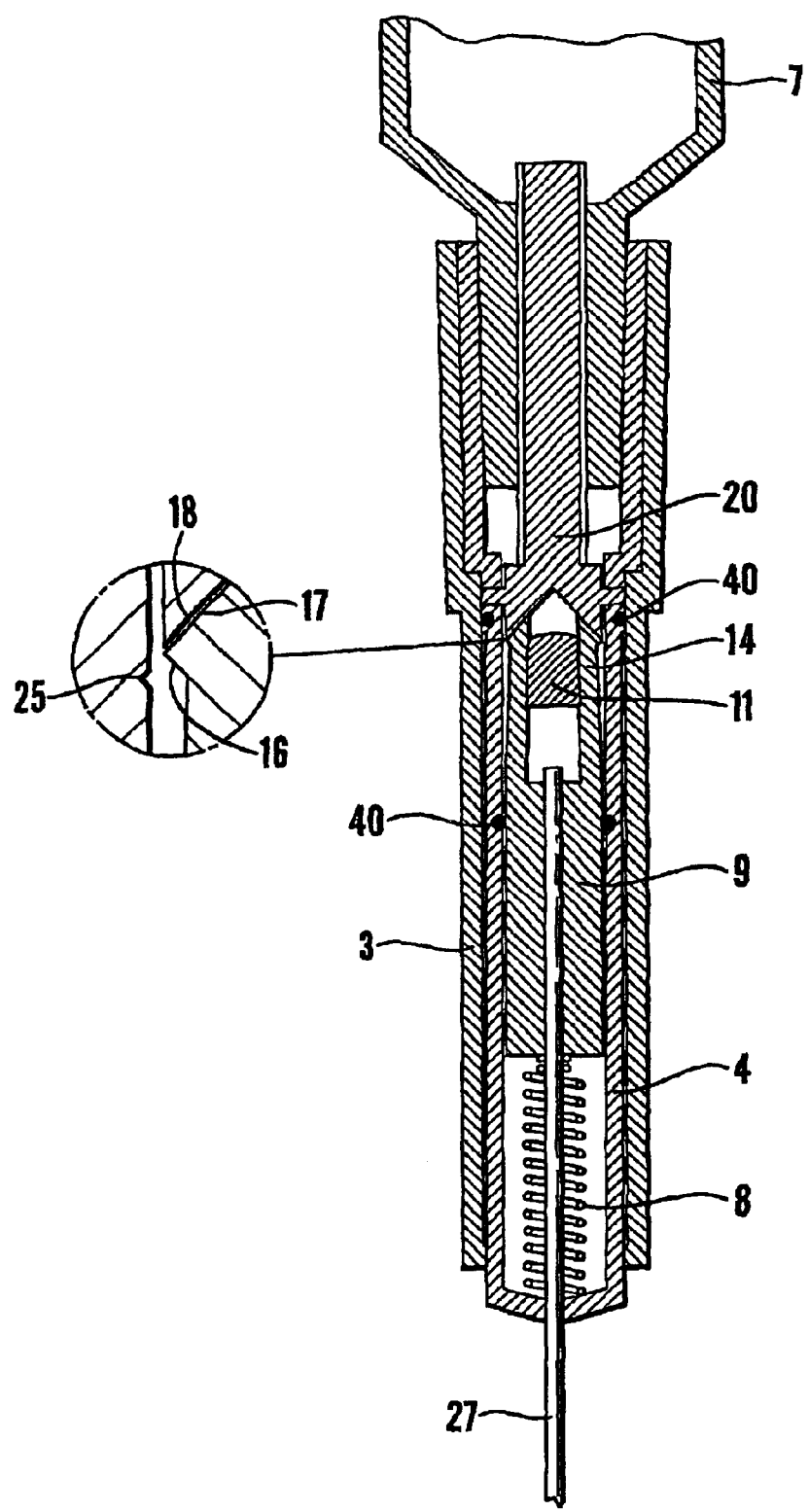
FIG. 6 is similar to FIG. 3, illustrating the beginning of an automatic release of the cover sleeve, FIG. 7 corresponds to FIG. 6, illustrating the cover sleeve in an extended position after the automatic release.

In FIG. 6 the spacer 11 has lost its mechanical strength, and has been deformed by compression forces from the first radially compressible portion 14, i.e. the first elastic arms, which are forced into the compressed position in the funnel-shaped portion 18 of the trigger 20 by the compression spring 8.

Figure 7:
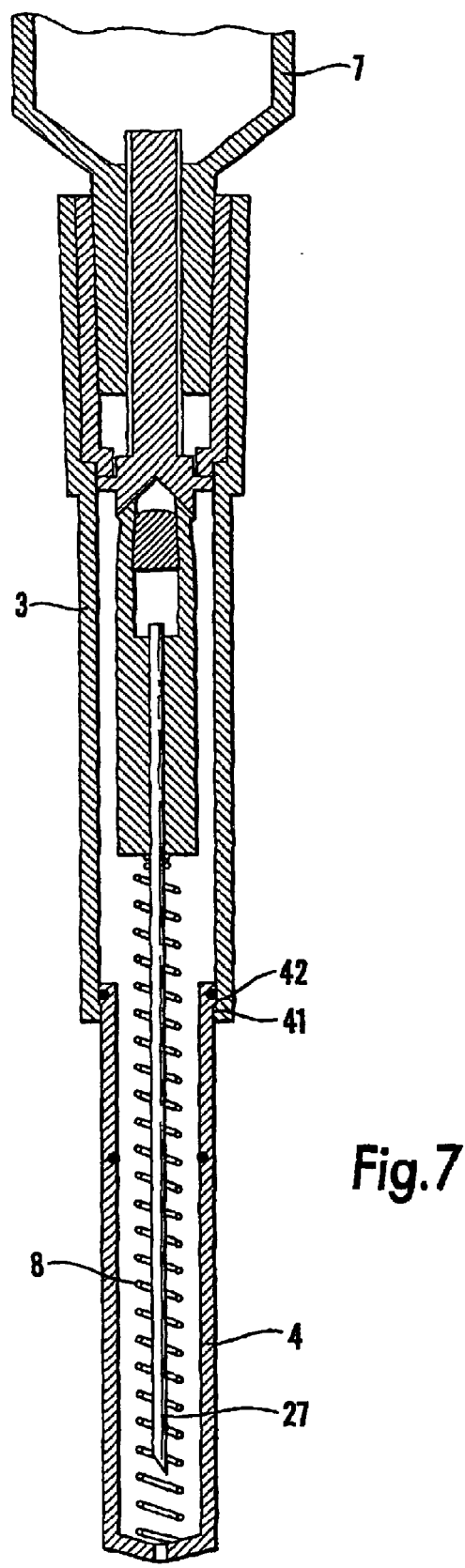

The first detents 16 then slip out of the indentations 25 in the cover sleeve 4, thereby releasing the cover sleeve 4 from the retracted position, and the spring 8 forces the cover sleeve 4 to the extended position, in which the needle 27 is covered, as illustrated in FIG. 7. It is thereby provided an automatic release of the needle covering mechanism.

Preferably the free ends 28 of the first elastic arms 14 have oblique end faces 17 corresponding to the funnel-shaped portion 18 of the trigger 20, as illustrated in FIG. 5, in order to facilitate the compression of the first elastic arms.

Figure 8:
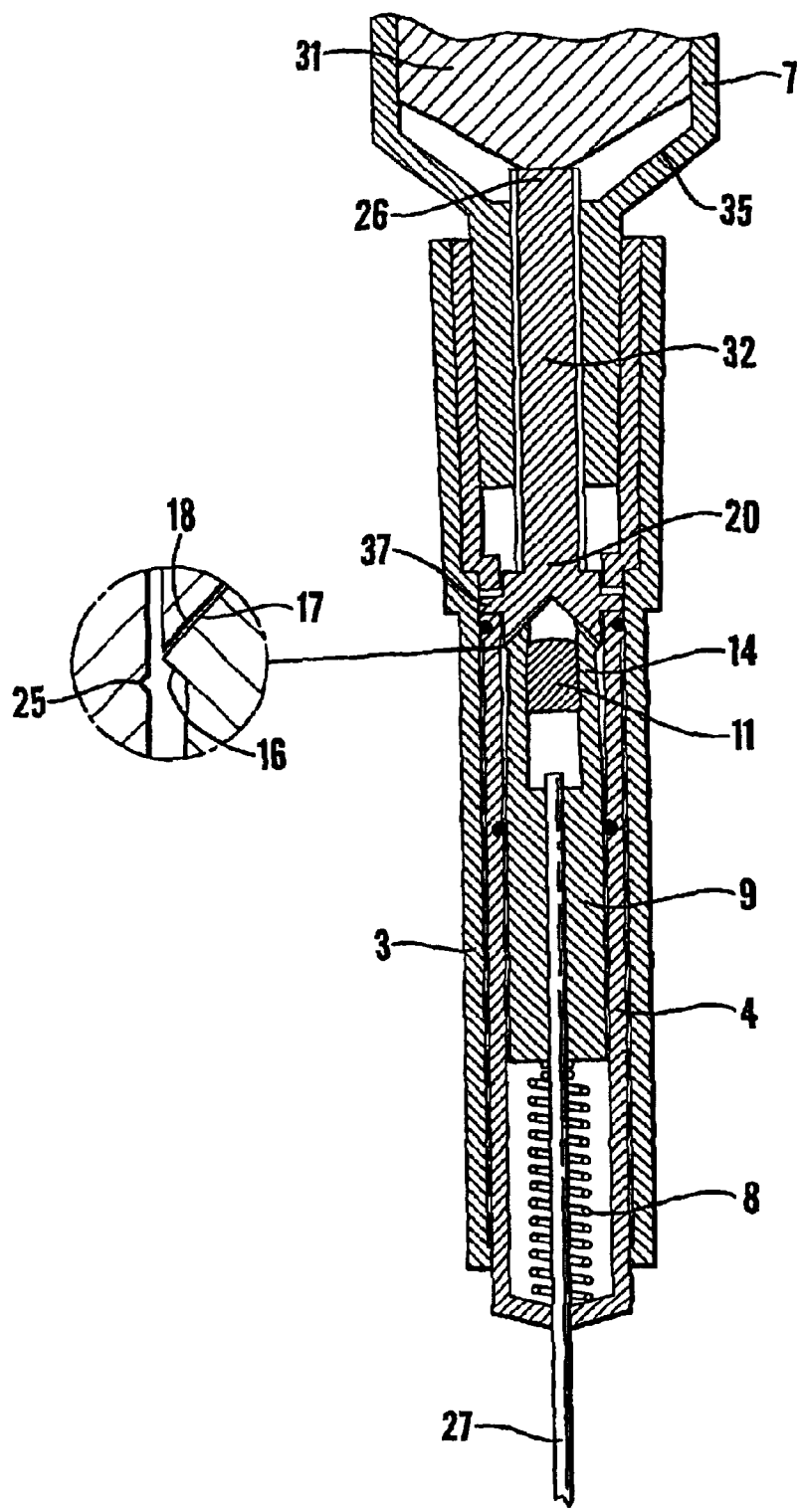
FIG. 8 is similar to FIG. 3, illustrating the beginning of a manual release of the cover sleeve.

Preferably the needle covering mechanism is also manually releasable, which is illustrated in FIG. 8. The trigger 20 comprises a head 26 which in an operating position of the mechanism 1 projects into the syringe barrel 7 and forms an abutment for the plunger 31 when the plunger is close to the bottom 35 of the barrel 7. A further movement of the plunger 31 towards the bottom 35 of the barrel 7, which is carried out by the syringe operator, moves the trigger 20 towards the retainer 9. The retainer 9 is kept in place by the second detents 22 being in engagement with the indentations 24 fixed relative to the body 3, see FIG. 4, and the funnel-shaped portion 18 of the trigger 20 thus forces the first compressible portion 14 of the retainer 9 into the compressed position. This causes an increase in the forces between the first compressible portion 14 and the spacer 11, which causes the spacer 11 to deform or break. The first detents 16 of the retainer 9 then slip out of the indentations 25 in the cover sleeve 4, thereby releasing the cover sleeve 4 from the retracted position. The spring 8 then forces the cover sleeve 4 to the extended position. It is thereby provided a manual release of the needle covering mechanism.

It is preferred, which is illustrated in FIG. 8, that when the needle covering mechanism is in its operating position, the end of the cover sleeve 4 which is closest to the trigger 20 abuts the trigger 20, namely the trigger guide 37. During a manual release the movement of the trigger 20 towards the retainer 9 thus causes the cover sleeve 4 to move towards the extended position, thereby assisting in releasing the cover sleeve 4 from the retracted position by forcing the first detents 16 out of the indentations 25 in the cover sleeve 4.

Figure 9:
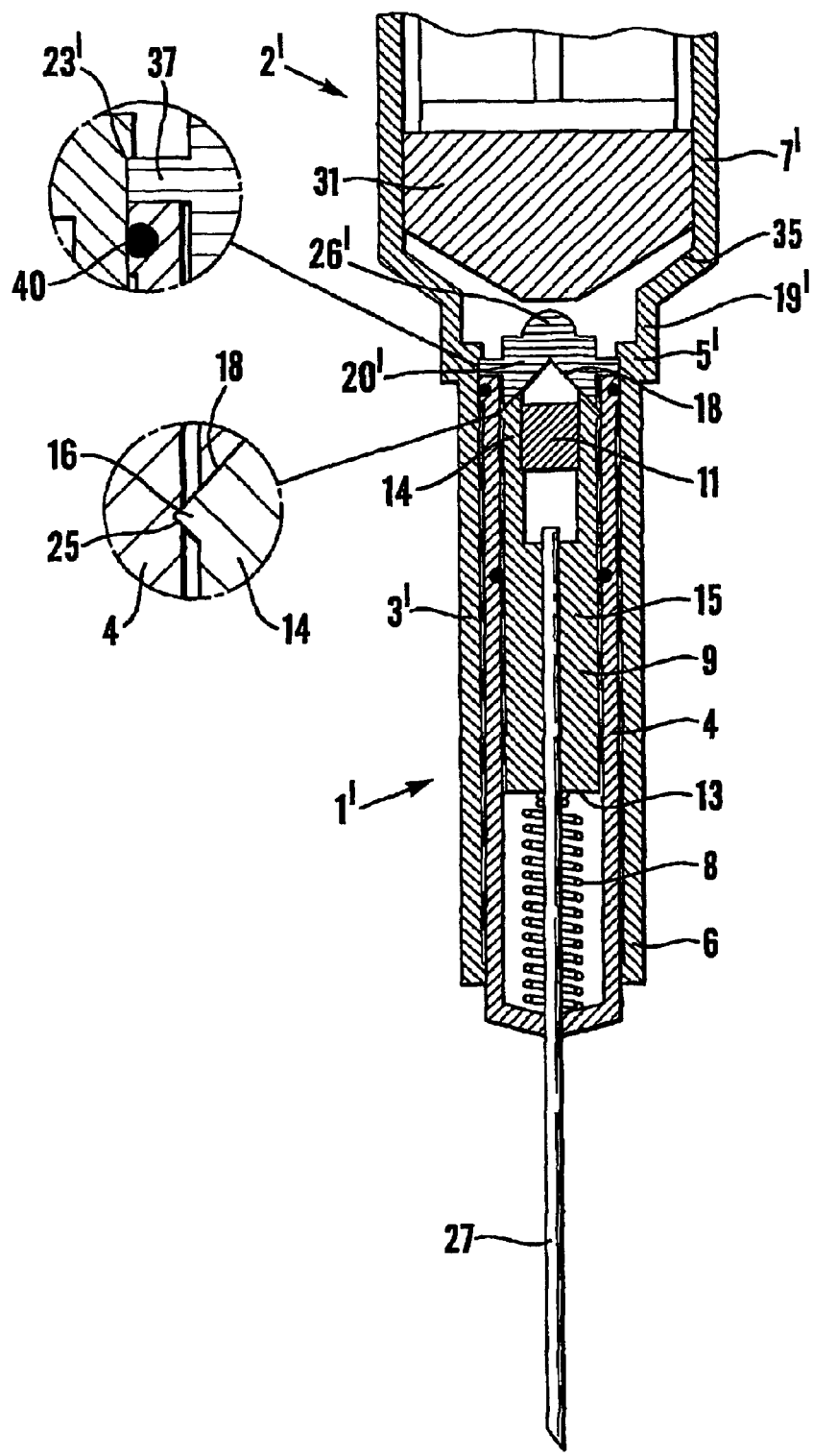
FIG. 9 illustrates a hypodermic syringe with an integrated needle covering mechanism according to the invention, with the cover sleeve in the retracted position.
Figure 10:
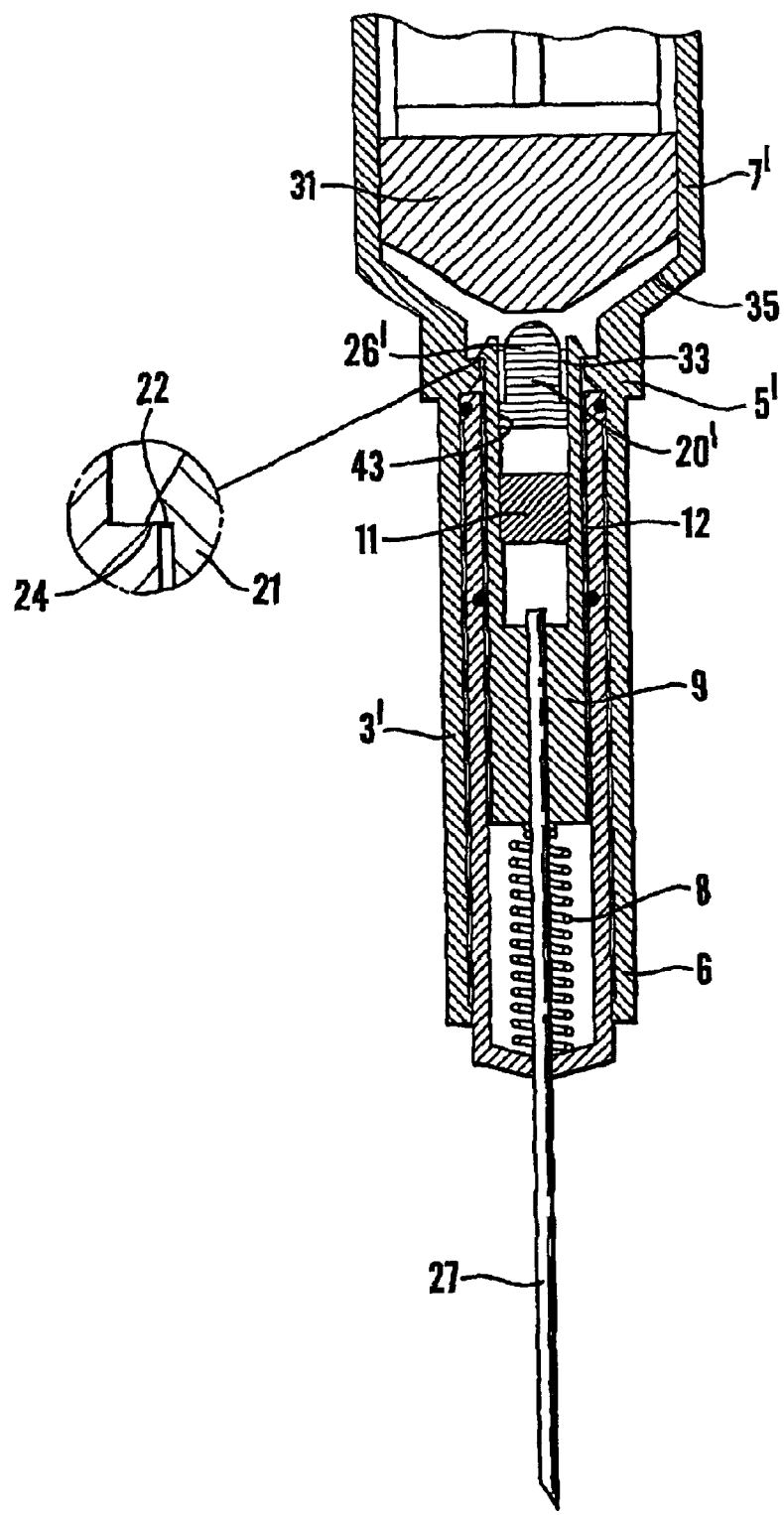
FIG. 10 illustrates the needle holder in FIG. 9 in a view perpendicular to the view of FIG. 9.

FIGS. 9 and 10 illustrates a hypodermic syringe 2' comprising a barrel 7' and a plunger 31, and a needle covering mechanism 1' according to the invention. The cover sleeve 4, the retainer 9, the spacer 11, the spring 8 and the needle 27 are as discussed above. In contrast to the above, the first end 5' of the body 3' does not form a part of a needle holder, but forms an integral extension of the outlet 19' of the barrel 7'. Further the outlet 19' of the syringe barrel 7' of the syringe 2' in FIGS. 9 and 10 is much wider and shorter than the outlet 19 of the syringe barrel of the syringe 2 discussed above, and consequently, in the needle covering mechanism 1' in FIGS. 9 and 10 there is no need for the rod 32 for forming the trigger head 26'. In the needle covering mechanism 1' in FIGS. 9 and 10 the trigger head 26' is therefore formed as a short, rounded end portion of the trigger 20'. In other respects the trigger 20' in FIGS. 9 and 10 is similar to the trigger 20 discussed above.

In FIG. 9, the stoppers 23' for the trigger guides 37 are formed by steps or shoulders in the first end 5' of the body 3'.

FIGS. 9 and 10 illustrates the mechanism 1' in its operating position, corresponding to FIGS. 3 and 4, respectively. The use of the syringe 2' in FIGS. 9 and 10 is similar to the use of the syringe 2 discussed above.

Figure 11:
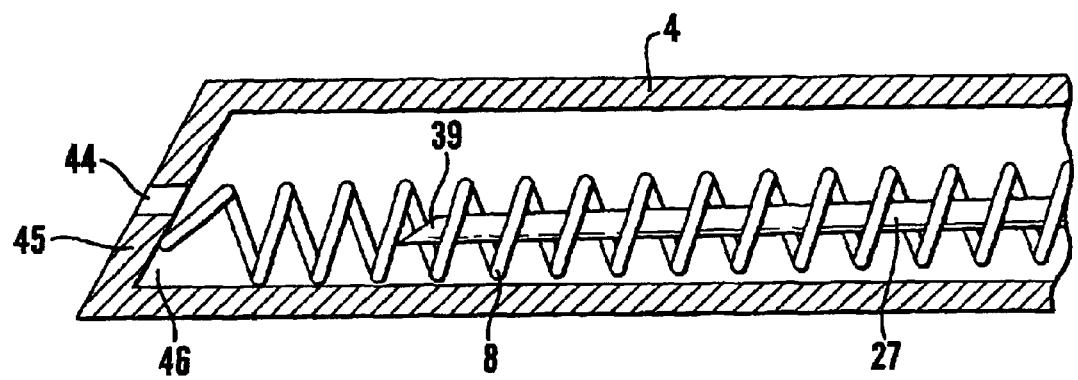
FIG. 11 illustrates an alternative cover sleeve according to the invention in an extended position.

FIG. 11 illustrates an alternative cover sleeve according to the invention in an extended position in which the needle 27 is covered. In this embodiment the cover sleeve 4 has an oblique end portion 45, which in an end area 46 form an acute angle with the cover sleeve's 4 cylindrical side. The compression spring 8 try to expand as much as possible, and therefore seeks to the end area 46. Consequently the spring 8 and also the needle 27 assumes an orientation pointing towards the end area 46. If, accidentally or intentionally, the cover sleeve 4 should be moved towards the retracted position, the spring 8 would be compressed and the needle tip 39 would hit the oblique end portion 45 in or close to the end area 46, instead of entering the opening 44. An increased protection is thereby established.

For practical purposes, the injectant is an aqueous solution. Alginate, in which algae is the main component, has favourable characteristica with respect to a predictable dissolving in water, and is therefore preferred as a material for the injectant responding spacer 11. Alginate is, however, a mechanically weak material. When producing the spacers, an aqueous alginate solution is moulded or extruded into the shape of the spacer, and the water is removed by applying heat and pressure to the alginate. By varying the composition of the alginate, and also the production method, spacers with various characteristica with respect to dissolving in water can be made. A particular interesting characteristic is the time from contact with the injectant until lost mechanical strength, or more precisely, the time from contact with the injectant until so much mechanical strength has been lost that the first detents 16 of the retainer 9 slip out of the first indentations 25 in the cover sleeve 4. The mechanical strength, both when dry and some time after contact with the injectant, is linked to the time from contact with the injectant until lost mechanical strength.

In the needle covering mechanism according to the invention, the injectant responding alginate item, i.e. the spacer 11, is subjected to forces from the first radially compressible portion of the retainer, which in turn are subjected to forces from the spring and forces from the funnel-shaped portion of the trigger. According to the laws of mechanics, a more acute angle of the funnel-shaped portion of the trigger causes bigger forces on the spacer, and a more obtuse angle of the funnel-shaped portion of the trigger causes smaller forces on the spacer. Thus, by adapting the angle of the funnel-shaped portion of the trigger, the needle covering mechanism can be adapted to a specific alginate which is favourable with respect to time from contact with the injectant until lost mechanical strength.

One reason why alginate has gained little use as the injectant responding item in automatic safety syringes is alginate's tendency to deform when subjected to forces for a long period. In the inventive mechanism, however, the spring is not tensioned until just before the syringe shall be used, and consequently the spacer is not subjected to forces until just before use. The invention thus enables the use of alginate in the spacer. The dissolving of alginate in water is reliable and predictable, and the invention thereby provides a reliable and predictable automatic needle covering mechanism.

Alternatively the spacer can be made from a water soluble polymer, e.g. chitosan, starch and modified starches, hyaluronic acid, guar, xanthan, cellulose acetate and other cellulose derivative or synthetic polymers e.g. polyvinyl alcohol, polyacrylic acid, polyacrylamide, polyesters and polyamines.

The needle can be a conventional steel needle, which may be fixed to the retainer by a tight fitting. The O-rings can be made from rubber, and the spring can be made from steel. Other principal items of the needle covering mechanism, the needle holder and the syringe according to the invention can be produced from plastic by moulding. Typical plastics include polycarbonate, acetal, polyoxymethylene, polypropylene and polyamide.

As an alternative to O-rings, sealing may be achieved by sealings which are co-injected with the cover sleeve, i.e. sealings which are injection moulded together with the cover sleeve. The co-injected sealings may be made from an elastic thermoplastic coplymer.

The needle covering mechanism according to the invention may be automatic only, which means that the trigger rod 32 and/or the trigger head 26 can be omitted. The needle covering mechanism according to the invention does, however, preferably also include the possibility of manual needle covering, as discussed above. The manual release may be used if a quick covering of the needle is preferred, or if the automatic release of the cover sleeve for some reason fails. The force which is required to deform or break the alginate during the manual release is moderate, as the alginate is weakened by the injectant. Thus the required force to produce a manual needle covering is also moderate.

The needle covering mechanism can be realised both in a separate needle holder, which has the advantage that it can be used with a wide range of syringes available on the market, and in a purpose designed syringe which has the advantage that no fitting of a separate needle holder is required prior to use, and that a re-use of the syringe by exchanging the needle holder is prevented.

What is claimed is:

1. A needle covering mechanism (1, 1') for a hypodermic syringe (2, 2') comprising a barrel (7, 7') for an injectant and a plunger (31) for expelling the injectant from the barrel (7, 7'), the needle covering mechanism (1, 1') comprises a protective cover sleeve (4) which is movable between a retracted position in which a needle (27) is exposed and an extended position in which the needle (27) is covered, a helical compression spring (8) located inside the cover sleeve (4) for biasing the cover sleeve (4) towards the extended position, a lock for keeping the cover sleeve (4) in the retracted position, and a release mechanism for releasing the lock, the needle covering mechanism (1, 1') is characterised by:

a body (3, 3') with a cover sleeve retraction chamber (10), which body (3, 3') in a first end (5, 5') is adapted to receive injectant from the barrel (7, 7') and in a second end (6) has an opening for the cover sleeve (4), the cover sleeve (4) being slidingly supported inside the body (3, 3'), enabling movement of the cover sleeve (4)

between the extended position and the retracted position essentially inside the retraction chamber (10), a retainer (9) for the cover sleeve (4), slidingly supported inside the cover sleeve (4), the retainer (9) comprises an external sliding surface (12), a base portion (15) for fixing and supporting the needle (27), an abutting potion (13) for the helical spring (8), a first radially compressible portion (14) with first detents (16) which in a non-compressed position projects radially out from the sliding surface (12) of the retainer (9) and in a compressed position are flush or within the sliding surface (12), a second radially compressible portion (21) with second detents (22) which in a non-compressed position projects radially out from the sliding surface (12) of the retainer (9) and in a compressed position are flush or within the sliding surface (12), a spacer (11) for maintaining the first radially compressible portion (14) of the retainer (9) in the non-compressed position, made from a material which after some time in contact with the injectant loses its mechanical strength, and a trigger (20, 20'), slidingly supported inside the body (3, 3'), comprising a funnel-shaped portion (18) facing the first radially compressible portion (14) of the retainer (9), wherein, in an operating position of the needle covering mechanism (1, 1'), the cover sleeve (4) is located essentially inside the retraction chamber (10) and the compression spring (8) is tensioned and biases the first radially compressible portion (14) of the retainer (9) towards the funnel-shaped portion (18) of the trigger (20, 20'), the trigger (20, 20') abuts stoppers (23, 23') fixed relative to the body (3, 3'), preventing a movement of the trigger (20, 20') towards the syringe barrel (7, 7'), the second detents (22) of the retainer (9) engage indentations (24) fixed relative to the body (3, 3'), preventing a movement of the retainer (9) away from the syringe barrel (7, 7'), and the first detents (16) of the retainer (9) engage indentations (25) in the cover sleeve (4), preventing a movement of the cover sleeve (4) towards the extended position, whereupon a contact between the spacer (11) and the injectant causes the spacer (11) to lose its mechanical strength and deform, the compression spring (8) forces the first radially compressible portion (14) of the retainer (9) into the funnel-shaped portion (18) of the trigger (20, 20') and thus into the compressed position, the first detents (16) slip out of the indentations (25) in the cover sleeve (4), thereby releasing the cover sleeve (4) from the retracted position, and the spring (8) forces the cover sleeve (4) to the extended position.

2. A needle covering mechanism (1, 1') according to claim 1, characterised in that the first radially compressible portion (14) of the retainer (9) comprises first elastic arms which extend from the base portion (15) of the retainer (9) and in their free ends (28) are moveable between the compressed and non-compressed position.

3. A needle covering mechanism (1, 1') according to claim 2, characterised in that the free ends (29) of the first elastic anus (14) have oblique end faces (17), corresponding to the funnel-shaped portion (18) of the trigger (20, 20'.

4. A needle covering mechanism (1, 1') according to claim 2, characterised in that the first elastic arms (14) have mountings (29) for the spacer (11).

5. A needle covering mechanism (1, 1') according to claim 2, characterised by two first elastic arms (14) and a spacer (11) formed by a bolt which is mounted between the first elastic arms (14).

6. A needle covering mechanism (1, 1') according to claim 1, characterized in that the trigger (20, 20') comprises a head (26, 26') which in the operating position of the needle covering mechanism (1, 1') projects into the syringe barrel (7, 7') and forms an abutment for the plunger (31) when the plunger (31) is close to the bottom (35) of the barrel (7, 7'), whereupon a further movement of the plunger (31) towards the bottom (35) of the barrel (7, 7') moves the trigger (20, 20') towards the retainer (9), causing the funnel-shaped portion (18) of the trigger (20, 20') to force the first compressible portion (14) of the retainer (9) into the compressed position, thereby deforming the spacer (11), the first detents (16) of the retainer (9) slip out of the indentations (25) in the cover sleeve (4), thereby releasing the cover sleeve (4) from the retracted position, and the spring (8) forces the cover sleeve (4) to the extended position.

7. A needle covering mechanism (1, 1') according to claim 6, characterized in that, in the operating position of the needle covering mechanism (1, 1'), the cover sleeve (4) abuts the trigger (20, 20'), whereupon a movement of the trigger (20, 20') towards the retainer (9) causes the cover sleeve (4) to move towards the extended position, thereby assisting in releasing the cover sleeve (4) from the retracted position by forcing the first detents (16) out of the indentations (25) in the cover sleeve (4).

8. A needle covering mechanism (1, 1') according to claim 1, wherein sealing between the cover sleeve (4) and the body (3) and retainer (9), respectively, is achieved by sealings which are co-injected with the cover sleeve (4).

9. A needle holder (34) for a hypodermic syringe (2) according to claim 8, characterised in that the trigger (20) comprises a rod (32) which in the operating position of the needle covering mechanism (1) extend through the barrel outlet (19), the end of the rod (32) forming the trigger head (26).

10. A needle holder (34) for a hypodermic syringe (2), characterised in comprising a needle covering mechanism (1) according to claim 1, in which the first end (5) of the body (3) is adapted to match an outlet (19) of a syringe barrel (7).

11. A needle holder (34) for a hypodermic syringe (2) according to claim 10, characterised in that the rod (32) is provided with splines (33) providing channels for the injectant.

12. A needle covering mechanism (1, 1') according to claim 1, wherein the spacer (11) is made from alginate.

13. A needle covering mechanism (1, 1') according to claim 1, wherein the spacer (11) is made from a water soluble polymer.

14. A needle covering mechanism (1, 1') according to claim 1, wherein the second radially compressible portion (21) of the retainer (9) comprises second elastic arms which extend from the base portion (15) of the retainer (9) and in their free ends (30) are moveable between the compressed and non-compressed position.

15. A hypodermic syringe (2') comprising a barrel (7') and a plunger (31), characterised in comprising a needle covering mechanism (1') according to claim 1, in which the first end (5') of the body (3') forms an integral extension of the barrel (7').

* * * * *